(12) United States Patent
Gallagher et al.

(10) Patent No.: US 8,129,397 B2
(45) Date of Patent: Mar. 6, 2012

(54) SUBSTITUTED THIENO[2,3-D]PYRIMIDINES AS AMPA MODULATORS

(75) Inventors: Michael Gerard Gallagher, Newhouse (GB); Craig C. Jamieson, Newhouse (GB); Amanda Jane Lyons, Newhouse (GB); John Kinnaird Ferguson Maclean, Newhouse (GB); Elizabeth Margaret Moir, Newhouse (GB)

(73) Assignee: MSD Oss B.V., Rahway, NJ (US)

(*) Notice: Subject to any disclaimer, the term of this patent is extended or adjusted under 35 U.S.C. 154(b) by 552 days.

(21) Appl. No.: 12/269,306

(22) Filed: Nov. 12, 2008

(65) Prior Publication Data

US 2009/0131455 A1 May 21, 2009

Related U.S. Application Data

(60) Provisional application No. 60/987,480, filed on Nov. 13, 2007.

(30) Foreign Application Priority Data

Nov. 13, 2007 (EP) ..................................... 07120603

(51) Int. Cl.
| | | |
|---|---|---|
| C07D 495/04 | (2006.01) | |
| A61K 31/519 | (2006.01) | |
| A61P 25/24 | (2006.01) | |
| A61P 25/28 | (2006.01) | |
| A61P 25/22 | (2006.01) | |
| A61P 25/18 | (2006.01) | |
| A61P 25/16 | (2006.01) | |

(52) U.S. Cl. ..................................... 514/260.1; 544/278
(58) Field of Classification Search .................. 544/278; 514/265.1, 260.1
See application file for complete search history.

(56) References Cited

FOREIGN PATENT DOCUMENTS

| WO | WO2005/040110 | 5/2005 |
| WO | WO2005/070916 | 8/2005 |
| WO | WO2009/062930 | 5/2009 |

OTHER PUBLICATIONS

Vippagunta, S.R., (Adv. Drug. Delivery Rev., 2001, 48, pp. 3-26).*
PCT International Search Report dated, mailed on Jun. 2, 2009 for related International Application No. PCT/EP2008/065306; 4 pages.
Hosni, H.M. et. al.; "Thienopyrimidines. Part III. Synthesis of novel substituted Thieno[2.3-d]pyrimidinone Derivatives and their condensed products with Molluscidial and Larcividial activities"; Journal of Chemical Research. Synopses, London, GB. No. 11, Jan. 1, 1999; pp. 646-647.
A. C. Arai, et. al.; "Benzamide-Type AMPA Receptor Modulators for Two Subfamilies with Distinct Modes of Action, The Journal of Pharmacology and Experimental Therapeutics", vol. 303, No. 3, 2002, pp. 1075-1085.
Pirotte, B., et. al. "4H-1,2,4-Pyridothiaziazine 1,1-Dioxides and 2,3-Dihydro-4H-1,2,4-Pyridothiazdiazine . . . ", Journal of Medicinal Chemistry, American Chem. Society, vol. 41, No. 16, Jul. 30, 1998,pp. 2946-2959.
Ornstein, et. al.; "Biarylpropylsulfonamides as Novel, Potent Potentiators of 2-Amino-3- . . .", Journal of Medicinal Chemistry, American Chemical Society, vol. 43, No. 23, Jan. 1, 2000, pp. 4354-4358.
Yamada, K.A.; "Therapeutic potential of positive AMPA Receptor Modulators in the treatment of neurological disease", Expert Opinion on Investigational Drugs, vol. 9, No. 4; Jan. 1, 2000; pp. 765-777.

* cited by examiner

*Primary Examiner* — Susanna Moore
(74) *Attorney, Agent, or Firm* — Susan L. Hess; Gerard M. Devlin

(57) ABSTRACT

The present invention relates to a heterocyclic derivative according to formula I

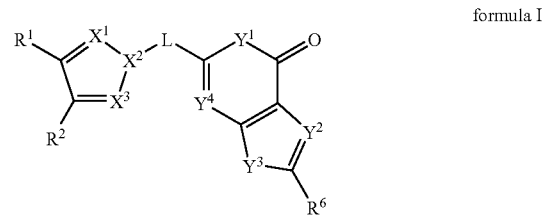

formula I wherein the variables are defined as in the specification, or to a pharmaceutically acceptable salt or solvate thereof. The present invention also relates to a pharmaceutical composition comprising said heterocyclic derivatives and to their use in therapy, for instance in the treatment or prevention of psychiatric diseases where an enhancement of synaptic responses mediated by AMPA receptors is required, including schizophrenia, depression and learning and memory disorders such as Alzheimer's disease.

15 Claims, No Drawings

SUBSTITUTED THIENO[2,3-D]PYRIMIDINES AS AMPA MODULATORS

RELATED APPLICATIONS

This application claims priority under 35 USC 119(e) from U.S. provisional application 60/987,480 filed Nov. 13, 2007.

FIELD OF THE INVENTION

The present invention relates to heterocyclic derivatives, to pharmaceutical compositions comprising these compounds and to their use in therapy, in particular to their use for the manufacture of a medicament for the treatment or prevention of psychiatric diseases where an enhancement of synaptic responses mediated by AMPA receptors is required, such as schizophrenia, depression and learning and memory disorders.

BACKGROUND OF THE INVENTION

L-glutamate is the most abundant excitatory neurotransmitter located in the mammalian central nervous system (CNS). L-glutamate plays a significant role in the control of cognition, mood and motor function and these processes are imbalanced in psychiatric and neurological disorders. The physiological effects of glutamate are mediated through two receptor families: the metabotropic (G-protein coupled) receptors and the ionotropic (ligand-gated ion channels) receptors. The ionotropic receptors are responsible for mediating the fast synaptic response to extracellular L-glutamate. The ionotropic glutamate receptors are separated into three subclasses on the basis of molecular and pharmacological differences and are named after the small molecule agonists which were originally identified to selectively activate them: AMPA (α-amino-3-hydroxy-5-methyl-4-isoxazole-propionic acid), NMDA (N-methyl-D-aspartate) and kainate (2-carboxy-3-carboxymethyl-4-isopropenylpyrrolidine).
The importance of AMPA receptors in brain physiology is widely recognised and it has been shown that AMPA receptors control the majority of fast excitatory amino acid transmission in the CNS and also contribute to synaptic plasticity playing a role in a variety of physiological processes such as learning and memory. To this end there has been a growing appreciation of the utility of positive allosteric modulators of the AMPA receptor for a variety of clinical indications including schizophrenia, depression and Alzheimer's disease.

AMPA receptor subunits are encoded by four distinct genes (termed GluR1 to 4), each representing proteins of around 900 amino acids. The individual sub-units consist of a large extracellular N-terminal domain, an extracellular ligand binding site for L-glutamate formed by domains designated S1 and S2. The transmembrane domain consists of three transmembrane regions, M1, M3 and M4 together with the re-entrant loop M2. This is then followed by a long intracellular C-terminal domain. All four AMPA receptor subunits contain so-called 'flip' and 'flop' splice variants which differ in alternate slicing of 38 amino acid encoding exons (differing by less than 10 amino acids) in the S2 extracellular domain. Further heterogeneity of the AMPA receptors results from RNA editing, the most significant being the Q/R site located in the pore region (M2) of the GluR2 subunit. The R variant, which a large proportion of native GluR2 subunits are believed to comprise, is characterised by significantly reduced calcium permeability. A further R/G editing site is located in the S2 domain of GluR2, GluR3 and GluR4 with the G form exhibiting an acceleration in the kinetics of recovery from desensitisation.

The kinetics of desensitisation and deactivation are important functional properties of the AMPA receptor that control the magnitude and duration of the synaptic response to glutamate. The processes of desensitisation and deactivation can be modulated by AMPA receptor positive allosteric modulators that bind remotely from the agonist binding site, yet influence agonist binding, or indeed agonist mediated conformational changes in the receptor associated with gating and/or desensitisation. Consequently there are continued efforts to develop drugs that specifically target these properties and which will have therapeutic potential in the treatment of a wide variety of CNS disorders associated with diminished glutamatergic signalling. These conditions include age-related memory impairment, Alzheimer's Disease, Parkinson's Disease, depression, psychosis, cognitive defects associated with psychosis, attention deficit disorder and attention deficit hyperactivity disorder.

A variety of structural classes of compounds are known which act as AMPA receptor modulators (see G. Lynch, *Current Opinion in Pharmacology*, 2006, 6, 82-88 for a recent review). For example, there are the so-called benzamide compounds related to aniracetam (see A. Arai et al., *J Pharmacol Exp. Ther.*, 2002, 30, 1075-1085), the benzothiadiazine derivatives such as S-18689 (see B. Pirotte, *J Med. Chem.*, 1998, 41, 2946-2959) and the biarylpropylsulfonamide derivatives (see P. L. Ornstein et al., *J Med. Chem.* 2000, 43, 4354-4358). Another class of AMPA receptor modulators was disclosed in International Patent Applications WO 2005/040110 and WO 2005/070916 which detail various heterocyclic compounds as being of utility as glutamate modulators. Compounds in each of these classes exhibit varying degrees of potentiation of the AMPA receptor.

Sustained AMPA receptor activation, however, is also associated with seizures and other proconvulsant side effects (Yamada K. A., *Exp. Opin. Invest. Drugs* 2000, 9, 765-777). Consequently there remains a need for further AMPA receptor modulators which have an optimal separation between beneficial therapeutic effects and unwanted neurotoxic effects.

*J. Chem. Res.*, 1999, 646 relates to the synthesis of novel substituted thieno[2,3-d]pyrimidione derivatives and their condensed products with molluscicidial and larvacidial activities. There is no suggestion, however that such compounds would be useful as AMPA receptor modulators.

DETAILED DESCRIPTION OF THE INVENTION

In a first aspect the present invention relates to a heterocyclic derivative according to formula I

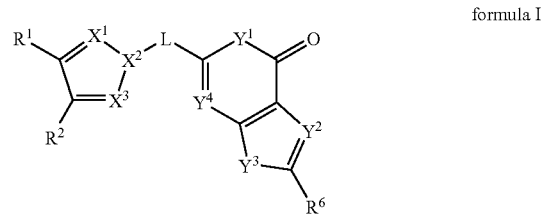

formula I wherein
L is $(CH_2)_m$, wherein m is 1 or 2;
$R^1$ is $C_{1-4}$alkyl, $C_{3-5}$cycloalkyl, $C_{1-4}$alkyloxy, halogen or CN, said $C_{1-4}$alkyl, $C_{3-5}$cycloalkyl and $C_{1-4}$alkyloxy being optionally substituted with one or more halogens;

$R^2$ is $C_{1-4}$alkyl, $C_{3-5}$cycloalkyl or $C_{1-4}$alkyloxy, said $C_{1-4}$alkyl, $C_{3-5}$cycloalkyl and $C_{1-4}$alkyloxy being substituted with a substituent selected from OH, $C_{1-4}$alkyloxy and $NR^9R^{10}$;

$X^1$—$X^3$ are independently N or $CR^3$, wherein $R^3$ is H or methyl;

$Y^1$ is $NR^4$ or $CHR^4$, wherein $R^4$ is H or $C_{1-4}$alkyl;

$Y^2$ is N or $CR^5$, wherein $R^5$ is H, $C_{1-4}$alkyl, $C_{3-8}$Cycloalkyl or $C_{6-10}$aryl;

$R^6$ is H, $C_{1-4}$alkyl or $C_{3-5}$cycloalkyl;

$Y^3$ is O, S or $NR^7$, wherein $R^7$ is H or $C_{1-4}$alkyl;

$Y^4$ is N or $CR^8$, wherein $R^8$ is H or $C_{1-4}$alkyl;

$R^9$ and $R^{10}$ are independently H or $C_{1-4}$alkyl optionally substituted with a 5-9 membered heteroaryl ring system comprising 1-2 heteroatoms selected from O, S and N, or $R^9$ and $R^{10}$ together with the N to which they are bonded form a 4-6 membered saturated or unsaturated heterocyclic ring optionally comprising another heteroatom selected from O, S and N or a pharmaceutically acceptable salt or solvate thereof.

The term $C_{1-4}$alkyl, as used herein, represents a branched or unbranched alkyl group having 1-4 carbon atoms. Examples of such groups are methyl, ethyl, isopropyl and tertiary butyl.

The term $C_{3-8}$cycloalkyl, as used herein, represents a branched or unbranched cyclic alkyl group having 3-8 carbon atoms. Examples of such groups are cyclopropyl, cyclopentyl and 2-methylcyclohexyl. Similarly the term $C_{3-5}$cycloalkyl, as used herein, represents a branched or unbranched cyclic alkyl group having 3-5 carbon atoms. Examples of such groups are cyclopropyl and cyclopentyl.

The term $C_{1-4}$alkyloxy, as used herein, represents a branched or unbranched alkyloxy group having 1-4 carbon atoms. Examples of such groups are methoxy, ethoxy, isopropyloxy and tertiary butyloxy.

The term $C_{6-10}$aryl, as used herein, represents an aromatic group having 6-10 carbon atoms and comprising one ring or two rings fused together, at least one of which must be aromatic. Examples of such groups include phenyl and naphthyl.

The term halogen, as used herein, represents a fluorine, chlorine, bromine or iodine.

Examples of 5 to 9 membered heteroaryl ring systems comprising 1-2 heteroatoms selected from O, S and N include, but are not limited to, furan, pyrrole, thiophene, imidazole, pyrrazole, thiazole, pyridine, pyrimidine, indole, indazole and benzthiophene.

Examples of 4 to 6 membered saturated or unsaturated heterocyclic rings optionally comprising another heteroatom selected from O, S and N include, but are not limited to, pyrrole, imidazole, pyrrazole, thiazole, pyridine piperidine morpholine and tetrahydropyridine.

The term solvate, as used herein, refers to a complex of variable stoichiometry formed by a solvent and a solute (in this invention, a compound of formula I). Such solvents may not interfere with the biological activity of the solute. Examples of suitable solvents include, but are not limited to, water, ethanol and acetic acid.

In one embodiment of the present invention, L is $CH_2$. In another embodiment, L is $(CH_2)_2$.

In a further embodiment of the present invention, $R^1$ is $C_{1-4}$alkyl, $C_{1-4}$alkyloxy, halogen or CN, said $C_{1-4}$alkyl and $C_{1-4}$alkyloxy being optionally substituted with one or more halogens. In a further embodiment, $R^1$ is $C_{1-4}$alkyl or CN, said $C_{1-4}$alkyl being optionally substituted with 1-3 halogens. In a further embodiment $R^1$ is isopropyl, tertiary butyl, CN or trifluoromethyl. In a further embodiment $R^1$ is trifluoromethyl.

In another embodiment of the present invention, $R^2$ is $C_{1-4}$alkyl substituted with a substituent selected from OH, $C_{1-4}$alkyloxy and $NR^9R^{10}$. In a further embodiment, $R^2$ is methyl optionally substituted with hydroxy, $C_{1-4}$alkyloxy or $NR^9R^{10}$, wherein $R^9$ and $R^{10}$ have the previously defined meanings. In a further embodiment $R^2$ is hydroxymethyl or $CH_2NR^9R^{10}$.

In another embodiment of the present invention, $X^1$ and $X^2$ are N and $X^3$ is $CR^3$, wherein $R^3$ has the previously defined meanings. In a further embodiment, $X^1$ and $X^2$ are N and $X^3$ is CH.

In another embodiment of the present invention, $X^1$ and $X^3$ are N and $X^2$ is $CR^3$, wherein $R^3$ has the previously defined meanings.

In another embodiment of the present invention, $X^1$ is $CR^3$ and $X^2$ and $X^3$ are N, wherein $R^3$ has the previously defined meanings.

In another embodiment of the present invention, $R^3$ is H or methyl. In a further embodiment, $R^3$ is H.

In another embodiment of the present invention, $Y^1$ is $NR^4$, wherein $R^4$ has the previously defined meanings.

In another embodiment of the present invention, $Y^2$ is N. In a further embodiment, $Y^2$ is $CR^5$, wherein $R^5$ has the previously defined meanings.

In another embodiment of the present invention, $Y^3$ is O or S. In a further embodiment, $Y^3$ is S. In a further embodiment, $Y^3$ is $CR^7$, wherein $R^7$ has the previously defined meanings.

In another embodiment of the present invention, $Y^4$ is N. In a further embodiment, $Y^4$ is $CR^8$, wherein $R^8$ has the previously defined meanings.

In another embodiment of the present invention, $R^4$ is H or $C_{1-4}$alkyl. In another embodiment, $R^4$ is H or methyl. In a further embodiment, $R^4$ is H. In a further embodiment, $Y^1$ is $NR^4$, wherein $R^4$ is H or methyl. In a further embodiment, $Y^1$ is $NR^4$, wherein $R^4$ is H.

In another embodiment of the present invention, $R^5$ is H, $C_{1-4}$alkyl, $C_{3-8}$cycloalkyl or $C_{6-10}$aryl. In a further embodiment, $R^5$ is H, methyl or phenyl. In a further embodiment $R^5$ is H or methyl. In a further embodiment, $Y^2$ is $CR^5$, wherein $R^5$ is H or methyl.

In another embodiment of the present invention, $R^6$ is H or $C_{1-4}$alkyl. In a further embodiment, $R^6$ is H or methyl;

In another embodiment of the present invention $R^7$ and $R^8$ are independently H or methyl. In a further embodiment, $R^7$ and $R^8$ are H.

In another embodiment of the present invention, $R^9$ and $R^{10}$ are independently H or $C_{1-4}$alkyl. In a further embodiment, $R^9$ and $R^{10}$ are independently H or $C_{1-4}$alkyl substituted with pyrrole, imidazole, thiazole, pyridine indole or indazole. In a further embodiment $R^9$ and $R^{10}$ are independently H or methyl substituted with pyrrole, imidazole, thiazole, pyridine, indole or indazole.

In a further embodiment of the present invention, $R^9$ and $R^{10}$ together with the N to which they are bonded form a piperidine, morpholine, pyrrole or imidazole ring.

In a further embodiment of the present invention, is a heterocyclic derivative according to formula II

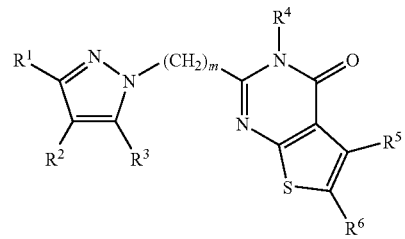

Formula II wherein $R^1$-$R^6$ and m have the previously defined meanings.

In a further embodiment of the present invention, is a heterocyclic derivative according to formula II

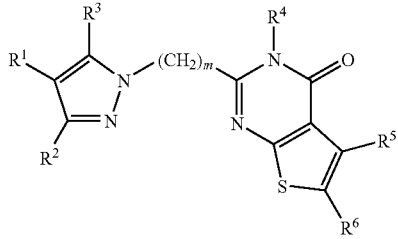

Formula III wherein $R^1$-$R^6$ and m have the previously defined meanings.

In a further embodiment of the present invention, is a heterocyclic derivative according to formula IV

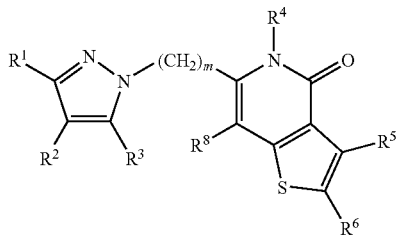

Formula IV wherein $R^1$-$R^6$, $R^8$ and m have the previously defined meanings.

In a further embodiment of the present invention, is a heterocyclic derivative according to formula V

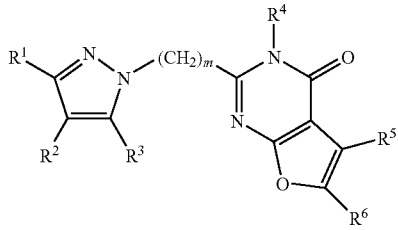

Formula V wherein $R^1$-$R^6$ and m have the previously defined meanings.

In another embodiment of the present invention is a heterocyclic derivative selected from:

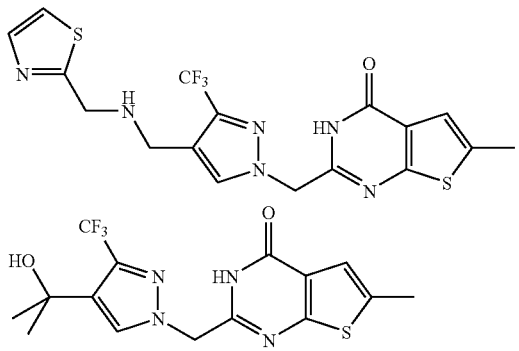

-continued

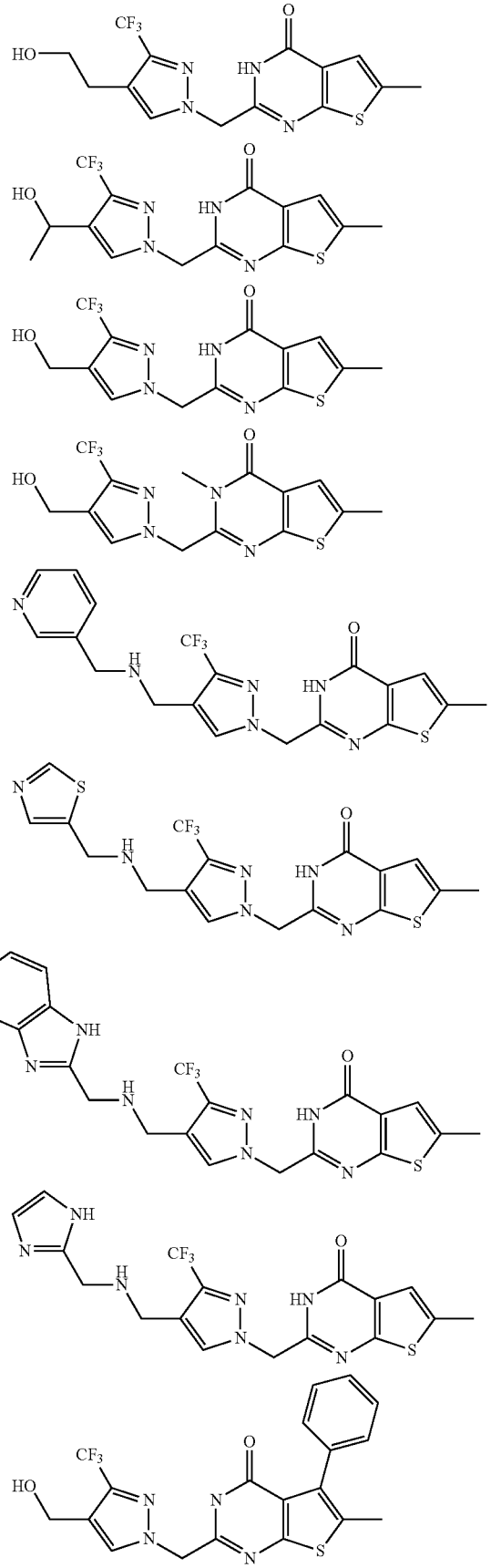

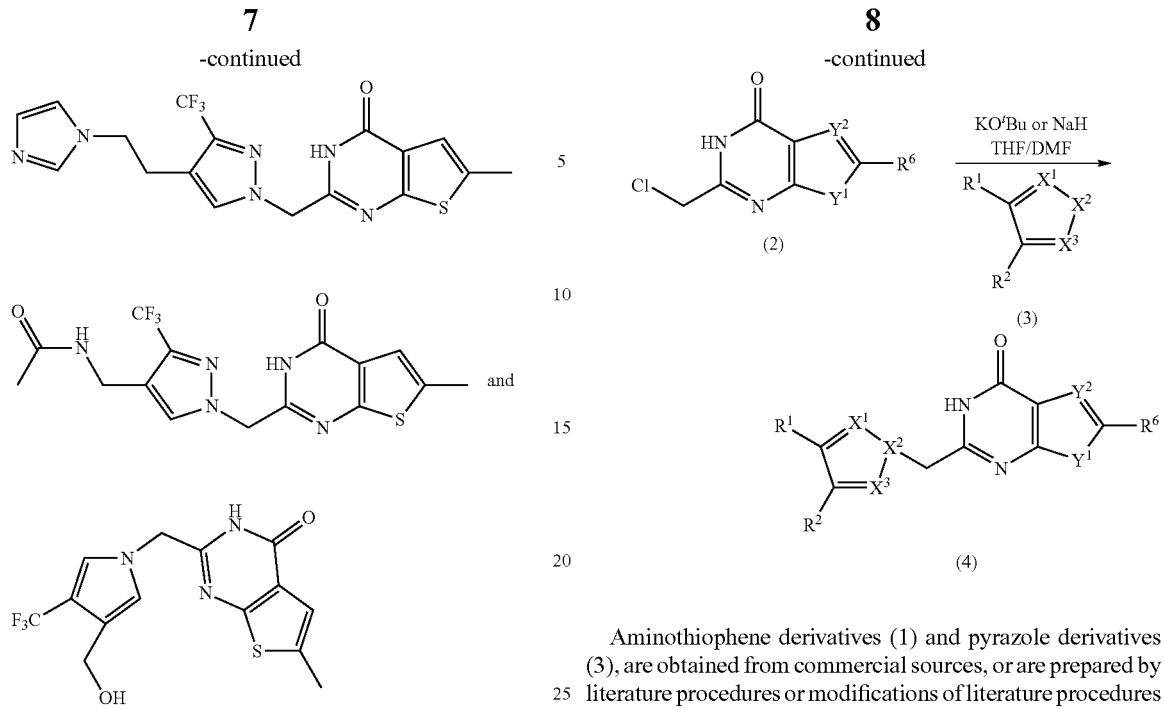

or a pharmaceutically acceptable salt or solvate thereof.

The heterocyclic derivatives of the present invention are prepared by methods well known in the art of organic chemistry. See, for example, J. March, 'Advanced Organic Chemistry' 4$^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts 'Protective Groups in Organic Synthesis' 2$^{nd}$ Edition, John Wiley and Sons, 1991. The protective groups are optionally removed at a convenient subsequent stage using methods well known in the art.

The synthesis of heterocyclic derivatives of the general formula (I) may be accomplished as outlined in Schemes 1-5 below.

Heterocyclic derivatives such as (4) are prepared as shown in Scheme 1. Treatment of the aminothiophene derivative (1) with chloroacetonitrile and HCl gas in a suitable solvent, for example dioxane, provides the chloromethyl derivatives (2). Further reaction of chloromethyl derivatives (2) with a pyrazole derivative (3) in the presence of a base, such as, potassium tert-butoxide in for example tetrahydrofuran (THF) and N,N-dimethylformamide (DMF) gives the adducts (4).

Aminothiophene derivatives (1) and pyrazole derivatives (3), are obtained from commercial sources, or are prepared by literature procedures or modifications of literature procedures known to persons skilled in the art. For example, as adumbrated in Scheme 2, aminothiophene derivatives (1) are prepared by the condensation of ethyl-2-cyanoacetate, ketone (5) and sulfur in the presence of an organic base such as diethylamine or N-methylmorpholine and in a suitable solvent such as ethanol.

Substituted azole derivatives may be prepared as illustrated in Scheme 3. Reductive amination of the aldehyde (7) using, for example, sodium triacetoxyborohydride and acetic acid in a suitable solvent such as N-methyl-2-pyrrolidinone (NMP), furnishes amine (8). Alternatively, treatment of the aldehyde (7) with a suitable Grignard reagent in a suitable solvent, such as diethyl ether, gives hydroxyalkyl derivative (9). Reduction of aldehyde (7) using, for example, sodium borohydride in a suitable solvent, such as dichloromethane and ethanol, provides alcohol (10). The heterocyclic core of (10) can be further elaborated by treatment with sodium hydride and iodomethane in a suitable solvent such as N,N-dimethylformamide (DMF), to give N-methyl analogue (11).

Scheme 3.

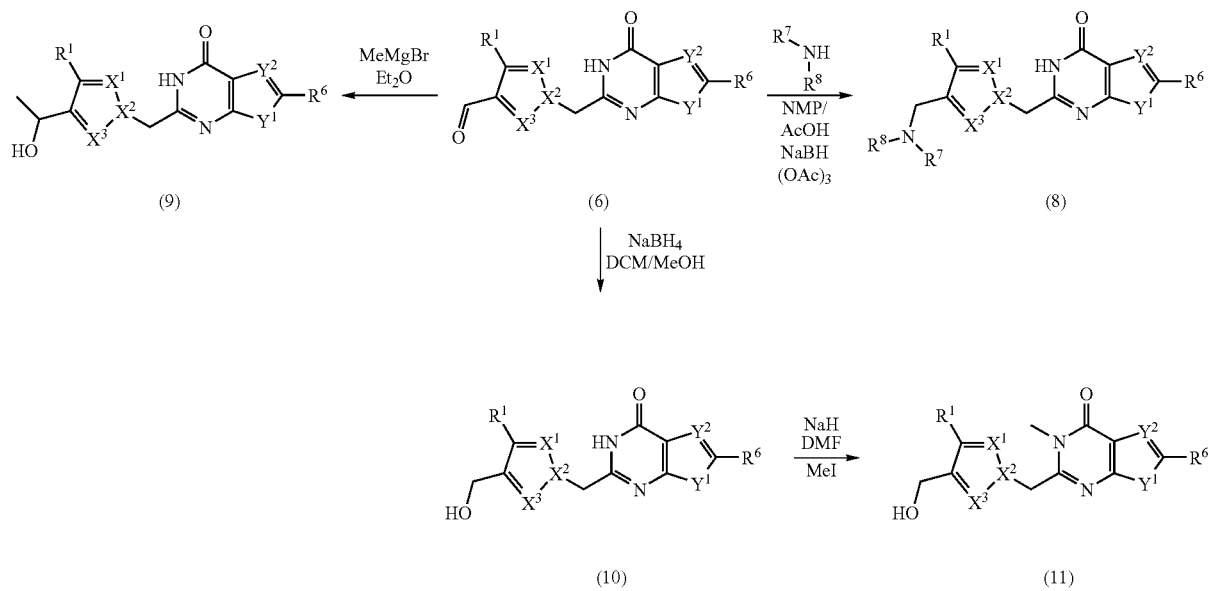

Aldehyde derivatives of the type (12) may be prepared as illustrated in Scheme 4. Reduction of esters of the type (13) with reagents such as lithium aluminium hydride in a suitable solvent, such as THF, gives alcohol (14). This is then followed by oxidation with manganese dioxide or a similar reagent, in for example acetonitrile, to provide aldehyde (13). Similarly, treatment of ester (13) with a suitable Grignard reagent, for example methyl magnesium bromide, in a suitable solvent, for example THF, gives the dialkyl alcohol (15).

Alkylamine derivatives of the type (19) can be prepared as delineated in Scheme 5. Treatment of chloromethyl derivative (2) with an alcohol (16) in the presence of a suitable base, e.g, potassium tertiary butoxide in, for example THF, provides intermediate (17). Conversion of the alcohol into a suitable leaving group, for example by reaction with methane sulphonyl chloride in, for example pyridine, followed by displacement with an amine in the presence of a suitable base and in a suitable solvent, for example in the presence of potassium Scheme 4.

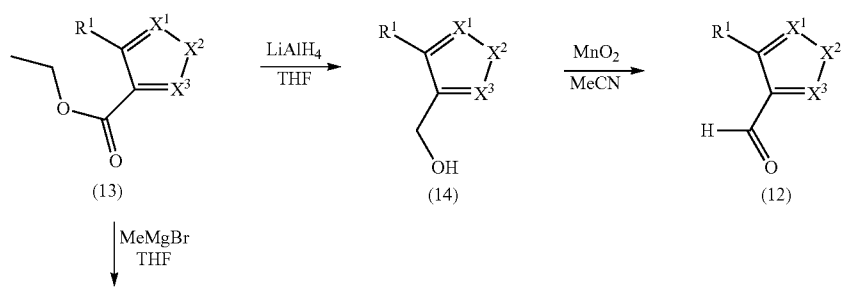

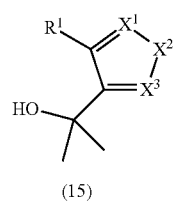

tertiary butoxide in dimethylsulphoxide, furnishes the desired alkyl amine derivative (19).

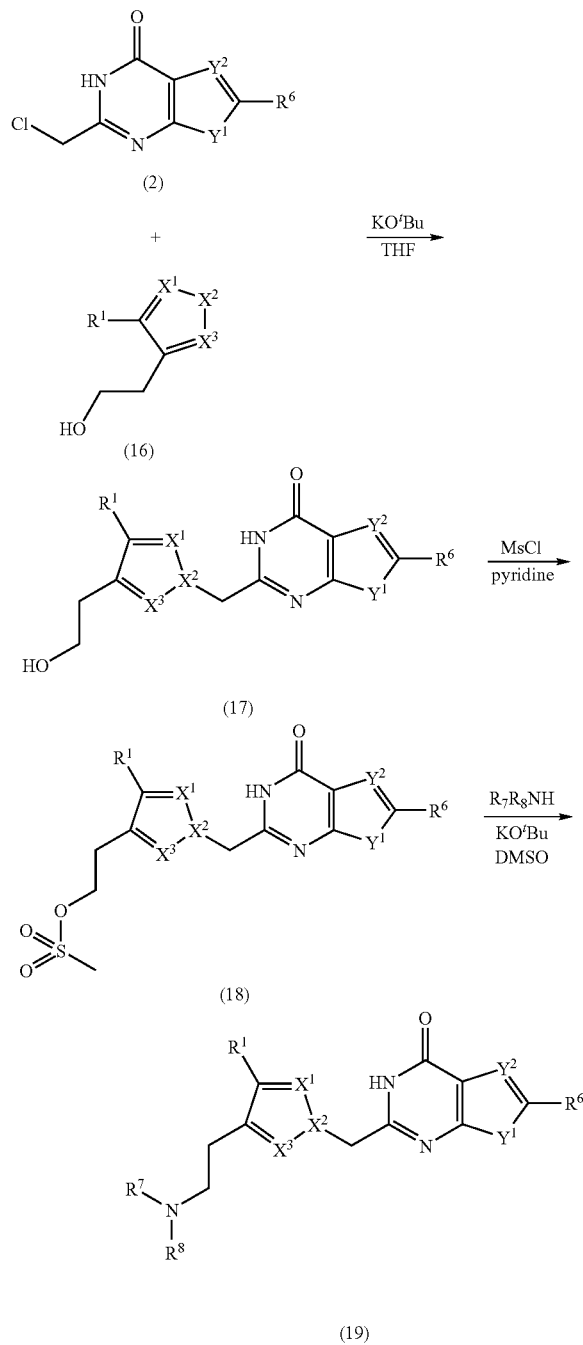

The present invention also includes within its scope all stereoisomeric forms of heterocyclic derivatives according to the present invention resulting, for example, because of configurational or geometrical isomerism. Such stereoisomeric forms are enantiomers, diastereoisomers, cis and trans isomers etc. For example, in the case where $R^2$ is 1-hydroxyethyl the compound exists as a pair of enantiomers. In the case of the individual stereoisomers of heterocyclic derivatives of formula I or salts or solvates thereof, the present invention includes the aforementioned stereoisomers substantially free, i.e., associated with less than 5%, preferably less than 2% and in particular less than 1% of the other stereoisomer. Mixtures of stereoisomers in any proportion, for example a racemic mixture comprising substantially equal amounts of two enantiomers are also included within the scope of the present invention.

For chiral compounds, methods for asymmetric synthesis whereby the pure stereoisomers are obtained are well known in the art, e.g., synthesis with chiral induction, synthesis starting from chiral intermediates, enantioselective enzymatic conversions, separation of stereoisomers using chromatography on chiral media. Such methods are described in *Chirality In Industry* (edited by A. N. Collins, G. N. Sheldrake and J. Crosby, 1992; John Wiley).

The heterocyclic derivatives of the present invention, in the form as a free base, are isolated from reaction mixtures as pharmaceutically acceptable salts. These salts are also obtained by treatment of said free base with an organic or inorganic acid. Examples of such acids include, but are not limited to, hydrogen chloride, hydrogen bromide, hydrogen iodide, sulfuric acid, phosphoric acid, acetic acid, trifluoroacetic acid, propionic acid, glycolic acid, maleic acid, malonic acid, methanesulfonic acid, fumaric acid, succinic acid, tartaric acid, citric acid, benzoic acid and ascorbic acid.

The heterocyclic derivatives of the present invention also exist as amorphous forms. Multiple crystalline forms are also possible. All these physical forms are also included within the scope of the present invention.

Preparation of Solvates is Generally Known. Thus, for Example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The present invention also embraces isotopically-labelled compounds of the compounds described and claimed herein which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labelled reagent for a non-isotopically labelled reagent.

Prodrugs of the compounds of the invention are also contemplated within the scope of the invention. A prodrug is a compound which acts as a drug precursor which, upon administration to a subject, undergoes conversion by metabolic or other chemical processes to yield a heterocyclic derivative of Formula I or a solvate or salt thereof. For example, where $X^1$ is NH the nitrogen group may be capped as, for example, an amide or carbamate which upon administration to a subject will undergo conversion back to the free hydroxyl group. A discussion of prodrugs is provided in T. Higuchi and V. Stella, *Prodrugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In a further aspect, the heterocyclic derivatives of the present invention and their pharmaceutically acceptable salts and solvates are useful in therapy. As such the heterocyclic derivatives of the present invention are useful for the manufacture of a medicament for the treatment or prevention of psychiatric diseases where an enhancement of synaptic responses mediated by AMPA receptors is required. In particular the heterocyclic derivatives are useful for the manufacture of a medicament for the treatment of neurodegenerative disorders, cognitive or memory dysfunction, memory and learning disorders, attention disorder, trauma, stroke, epilepsy, Alzheimer's disease, depression, schizophrenia, psychotic disorders, anxiety, autism, a disorder or disease resulting from neurotic agents, substance abuse, alcohol psychiatric disorders, Parkinson's Disease, sleep disorders or narcolepsy or other conditions resulting from sleep deprivation. The present invention further includes a heterocyclic derivative for use in the treatment of any of the aforementioned diseases or disorders.

The present invention further includes a method for the treatment of a mammal, including a human, suffering from or liable to suffer from depression or any of the aforementioned disorders, which comprises administering an effective amount of a heterocyclic derivative according to the present invention or a pharmaceutically acceptable salt or solvate thereof to a subject in need thereof. By effective amount or therapeutically effective amount is meant an amount of compound or a composition of the present invention effective in inhibiting the above-noted diseases and thus producing the desired therapeutic, ameliorative, inhibitory or preventative effect.

The amount of a heterocyclic derivative of the present invention or a pharmaceutically acceptable salt or solvate thereof, also referred to herein as the active ingredient, which is required to achieve a therapeutic effect will, of course, vary with the particular compound, the route of administration, the age and condition of the recipient and the particular disorder or disease being treated.

A suitable daily dose for any of the above mentioned disorders will be in the range of 0.001 to 50 mg per kilogram body weight of the recipient (e.g. a human) per day, preferably in the range of 0.01 to 20 mg per kilogram body weight per day. The desired dose may be presented as multiple sub-doses administered at appropriate intervals throughout the day.

Whilst it is possible for the active ingredient to be administered alone, it is preferable to present it as a pharmaceutical composition. The present invention therefore also provides a pharmaceutical composition comprising a heterocyclic derivative according to the present invention in admixture with one or more pharmaceutically acceptable excipients, such as the ones described in Gennaro et al., Remmington: *The Science and Practice of Pharmacy*, 20th Edition, Lippincott, Williams and Wilkins, 2000; see especially part 5: pharmaceutical manufacturing. The term "acceptable" means being compatible with the other ingredients of the composition and not deleterious to the recipients thereof. Suitable excipients are described e.g., in the Handbook of Pharmaceutical Excipients, 2nd Edition; Editors A. Wade and P. J. Weller, American Pharmaceutical Association, Washington, The Pharmaceutical Press, London, 1994. Compositions include those suitable for oral, nasal, topical (including buccal, sublingual and transdermal), parenteral (including subcutaneous, intravenous and intramuscular) or rectal administration.

The mixtures of a heterocyclic derivative according to the present invention and one or more pharmaceutically acceptable excipient or excipients may be compressed into solid dosage units, such as tablets, or be processed into capsules or suppositories. By means of pharmaceutically suitable liquids the compounds can also be applied as an injection preparation in the form of a solution, suspension, emulsion, or as a spray, e.g., a nasal or buccal spray. For making dosage units e.g., tablets, the use of conventional additives such as fillers, colorants, polymeric binders and the like is contemplated. In general, any pharmaceutically acceptable additive can be used. The compounds of the invention are also suitable for use in an implant, a patch, a gel or any other preparation for immediate and/or sustained release.

Suitable fillers with which the pharmaceutical compositions can be prepared and administered include lactose, starch, cellulose and derivatives thereof, and the like, or mixtures thereof used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The present invention further includes a pharmaceutical composition, as hereinbefore described, in combination with packaging material suitable for said composition, said packaging material including instructions for the use of the composition for the use as hereinbefore described.

The invention is further illustrated by the following examples which are not intended to limit the scope thereof.

EXAMPLE 1

6-Methyl-2-((4-(((thiazol-2-ylmethylamino)methyl)-3-(trifluoromethyl)-1H-pyrazol-1-yl)methyl)thieno[2,3-d]pyrimidin-4(3H)-one a) (3-(Trifluoromethyl)-1H-pyrazol-4-yl)methanol

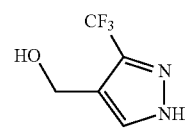

Ethyl 3-(trifluoromethyl)-1H-pyrazole-4-carboxylate (95.00 g, 0.456 mol) was dissolved in dry THF (1 L) and the resulting solution cooled in an acetone/ice bath. A 1M solution of LiAlH$_4$ in THF (550 mL, 0.550 mol) was added over 30 min, keeping the temperature <10° C. Cooling was then removed and the reaction mixture was stirred at RT for 4 h. The reaction was again cooled and a 1:1 THF:water solution (250 mL) was added with cooling (maintaining the temperature <20° C.), followed by 5M HCl (160 mL) to neutrality/pH 6. EtOAc (1.5 L) was added and the mixture stirred for 30 min then left to settle overnight. The resulting grey granular solid was removed by filtration through dicalite and washed with EtOAc. The combined filtrates were washed with brine and dried over MgSO$_4$, before concentrating in vacuo to give a white solid (76.00 g, 0.457 mol, 100%).

1H NMR (400 MHz, CD$_3$OD): δ 4.61 (s, 2H), 7.75 (s, 1H)

b) 3-(Trifluoromethyl)-1H-pyrazole-4-carbaldehyde

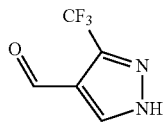

(3-(Trifluoromethyl)-1H-pyrazol-4-yl)methanol (54.00 g, 0.325 mol) was suspended in toluene (2 L). MnO$_2$ (113.00 g, 1.30 mol) and 4 Å molecular sieve powder (54.00 g) were added. The reaction mixture was stirred at reflux under nitrogen with a Dean-Stark trap for 5.5 h. The resulting mixture was filtered hot and the cake allowed to cool before washing with 1:1 DCM:MeOH solution (3×500 mL). The combined filtrates were concentrated in vacuo to give the desired product (54.00 g, 0.329 mol, 100%).

1H NMR (400 MHz, DMSO): δ 8.72 (s, 1H), 9.91 (s, 1H)

c) Ethyl 2-amino-5-methylthiophene-3-carboxylate

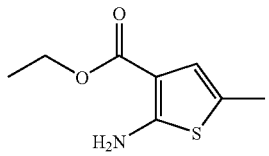

A stirred mixture of propionaldehyde (29.00 g, 0.499 mol), ethyl-2-cyanoacetate (56.50 g, 0.499 mol) and sulfur (15.98 g, 0.499 mol) in ethanol (275 mL) was heated to 65° C. over 30 min whilst diethylamine (36.50 g, 0.499 mol) was added dropwise. The mixture was stirred at 65° C. for 18 h and then concentrated in vacuo. Purification by flash column chromatography-silica gel and elution with 10% EtOAc:isohexane gave the desired product as a yellow oil (69.00 g, 0.372 mol, 75%).

MS (ESI): m/z 186 [M+H]$^+$.

d) 2-(Chloromethyl)-6-methylthieno[2,3-d]pyrimidin-4(3H)-one

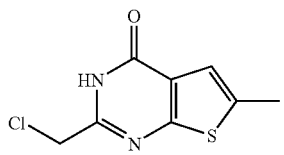

HCl gas was bubbled through a stirred mixture of ethyl 2-amino-5-methylthiophene-3-carboxylate (69.00 g, 0.372 mol) and chloroacetonitrile (33.70 g, 0.447 mol) in dioxane (600 mL) for 6 h. The mixture was then concentrated in vacuo to approximately 100-mL volume, poured onto water (1 L) and the mixture basified with NH$_4$OH. Filtration and oven drying gave a grey solid (approximately 60 g). The crude material was suspended in dioxane (1 L) and heated to reflux for 2 h before concentration in vacuo. This gave the title compound as a grey solid (57.88 g, 0.270 mol, 72%).

MS (ESI): 216 m/z [M+H]$^+$.

e) 1-((6-Methyl-4-oxo-3,4-dihydrothieno[2,3-d]pyrimidin-2-yl)methyl)-3-(trifluoromethyl)-1H-pyrazole-4-carbaldehyde

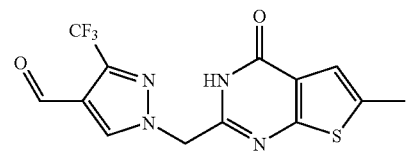

3-(Trifluoromethyl)-1H-pyrazole-4-carbaldehyde (3.82 g, 23.3 mmol) and 2-(chloromethyl)-6-methylthieno[2,3-d]pyrimidin-4(3H)-one (5.00 g, 23.3 mmol) were suspended in THF:DMF (180 mL:20 mL) and potassium tert-butoxide (5.23 g, 46.6 mmol) added. The resulting mixture was stirred at RT for 18 h. The mixture was then diluted with EtOAc (500 mL) and shaken with water (200 mL). The separated aqueous phase was acidified to pH 5 with dilute HCl solution and reshaken with the organic layer. The separated organics were then washed with brine (2×200 mL) and dried over MgSO$_4$ before concentration in vacuo. Purification by flash column chromatography-silica gel and elution with 50% isohexane:EtOAc, then EtOAc, gave the desired product as a pale yellow solid (4.65 g, 13.6 mmol, 58%).

MS (ESI): 341 m/z [M−H]$^-$.

f) 6-Methyl-2-((4-((thiazol-2-ylmethylamino)methyl)-3-(trifluoromethyl)-1H-pyrazol-1-yl)methyl)thieno[2,3-d]pyrimidin-4(3H)-one

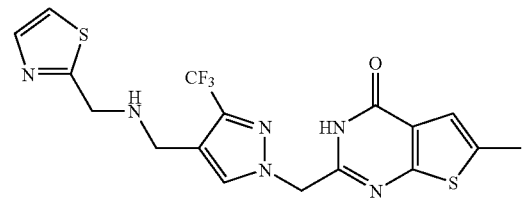

A mixture of 1-((6-methyl-4-oxo-3,4-dihydrothieno[2,3-d]pyrimidin-2-yl)methyl)-3-(trifluoromethyl)-1H-pyrazole-4-carbaldehyde (0.55 g, 1.62 mmol) and thiazol-2-ylmethanamine (925 mg, 8.10 mmol) in DCM (11 mL) was acidified to pH 5 with acetic acid (1 mL) before the addition of sodium triacetoxyborohydride (1.72 g, 8.10 mmol). The resultant mixture was stirred at RT overnight. The reaction mixture was quenched with MeOH, passed through an SCX column and eluted with 2M NH$_3$ in MeOH. The sample was concentrated in vacuo. Purification by flash column chromatography-silica gel and elution with 3-5% MeOH:DCM (3 drops of DIPEA per litre), followed by a second flash column and elution with 3-4% MeOH:DCM (3 drops of DIPEA per litre) gave the title product as a white solid (172 mg, 0.391 mmol, 24%).

MS (ESI): 441 m/z [M+H]$^+$.

EXAMPLE 2

2-((4-(2-Hydroxypropan-2-yl)-3-(trifluoromethyl)-1H-pyrazol-1-yl)methyl)-6-methyl thieno[2,3-d]pyrimidin-4(3H)-one a) 2-(3-(Trifluoromethyl)-1H-pyrazol-4-yl)propan-2-ol

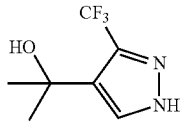

To a stirred solution of ethyl 3-(trifluoromethyl)-1H-pyrazole-4-carboxylate (649 mg, 3.12 mmol) in THF (6.50 mL) was added methylmagnesium bromide (2.57 g, 21.5 mmol) dropwise over 15 min such that the temperature remained at or below 0° C. The reaction mixture was stirred overnight and allowed to come to RT. Analysis at this stage showed the presence of unreacted starting material. The reaction mixture was cooled once more to <10° C. and more methylmagnesium bromide (2.57 g, 21.5 mmol) was added dropwise over 15 min and the resultant white suspension was stirred for a further 24 h. The reaction mixture was cooled to −5° C. and quenched with saturated NH$_4$Cl solution. The mixture was concentrated in vacuo and the residue partitioned between diethyl ether and water. The organic layer was separated, washed with saturated brine (×2), dried over MgSO$_4$, filtered and concentrated in vacuo to give the crude product as a yellow oil which partially solidified on standing. Purification by flash column chromatography-silica gel and elution with 40% EtOAc:isohexane gave the title product as a white solid (417 mg, 2.149 mmol, 69%).

MS (ESI): 193 m/z [M−H]$^-$.

b) 2-((4-(2-Hydroxypropan-2-yl)-3-(trifluoromethyl)-1H-pyrazol-1-yl)methyl)-6-methyl thieno[2,3-d]pyrimidin-4(3H)-one

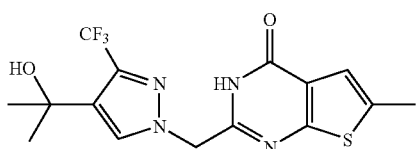

A mixture of 2-(3-(trifluoromethyl)-1H-pyrazol-4-yl)propan-2-ol (73 mg, 0.376 mmol) and potassium tert-butoxide (127 mg, 1.13 mmol) in THF (2 mL) was stirred for ~2 min. To this was added 2-(chloromethyl)-6-methylthieno[2,3-d]pyrimidin-4(3H)-one (81 mg, 0.376 mmol) and the resultant mixture was stirred for 18 h. The reaction mixture was quenched with saturated NH$_4$Cl solution and concentrated in vacuo. The residue was partitioned between DCM and water and the organic layer was separated. The aqueous layer was extracted with further DCM and the combined organics were washed with saturated brine, dried over MgSO$_4$, filtered and concentrated in vacuo to give a light yellow gum. The gum was purified by preparative LCMS to give the product as a white solid (5 mg, 0.014 mmol, 4%).

MS (ESI): 371 m/z [M−H]$^-$.

EXAMPLE 3

2-((4-(2-Hydroxyethyl)-3-(trifluoromethyl)-1H-pyrazol-1-yl)methyl)-6-methylthieno[2,3-d]pyrimidin-4(3H)-one

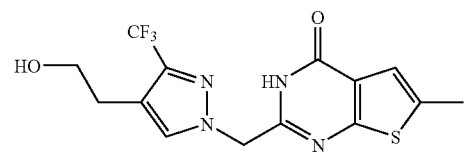

A mixture of 2-(3-(trifluoromethyl)-1H-pyrazol-4-yl)ethanol (50 mg, 0.278 mmol), 2-(chloromethyl)-6-methylthieno[2,3-d]pyrimidin-4(3H)-one (60 mg, 0.278 mmol) and potassium tert-butoxide (62 mg, 0.07 mL, 0.555 mmol) in THF (3 mL) was heated to 75° C. for 4 h. The reaction mixture was allowed to cool to RT before being filtered and concentrated in vacuo. The residue was purified by preparative reverse phase HPLC to give the title compound as a white solid (32 mg, 0.089 mmol, 32%).

MS (ESI): 359 m/z [M+H]$^+$.

EXAMPLE 4

2-((4-(1-Hydroxyethyl)-3-(trifluoromethyl)-1H-pyrazol-1-yl)methyl)-6-methylthieno[2,3-d]pyrimidin-4(3H)-one

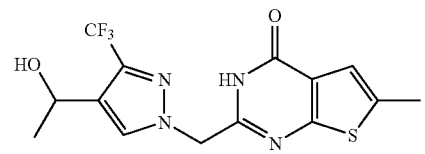

1-((6-Methyl-4-oxo-3,4-dihydrothieno[2,3-d]pyrimidin-2-yl)methyl)-3-(trifluoromethyl)-1H-pyrazole-4-carbaldehyde (100 mg, 0.292 mmol) was dissolved in diethyl ether (10 mL) and cooled to −78° C. with a dry ice/acetone bath. The reaction was performed under a nitrogen atmosphere. Methylmagnesium bromide (35 mg, 0.292 mmol) was added dropwise and the reaction mixture allowed to warm to RT and stirred for 2 h. Water was added and the reaction mixture extracted into EtOAc (×3). The combined EtOAc layers were washed with brine, dried over MgSO$_4$, filtered and concentrated in vacuo. Purification by preparative reverse phase HPLC gave the title product (8 mg, 0.023 mmol, 8%).

MS (ESI): 359 m/z [M+H]$^+$.

EXAMPLE 5

2-((4-(Hydroxymethyl)-3-(trifluoromethyl)-1H-pyrazol-1-yl)methyl)-6-methylthieno[2,3-d]pyrimidin-4(3H)-one

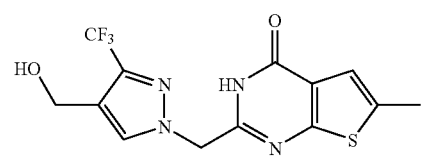

1-((6-Methyl-4-oxo-3,4-dihydrothieno[2,3-d]pyrimidin-2-yl)methyl)-3-(trifluoromethyl)-1H-pyrazole-4-carbaldehyde (100 mg, 0.292 mmol) was dissolved in a 1:1 DCM:MeOH solution (2 mL) and sodium borohydride (33 mg, 0.876 mmol) added. After 30 min the mixture was quenched by addition of water (1 mL) then concentrated in vacuo. Purification by flash column chromatography-silica gel and elution with 3% MeOH:DCM resulted in a white solid which was recrystallised from isopropanol and freeze dried to give the title compound as a white solid (28 mg, 0.081 mmol, 28%).

MS (ESI): 343 m/z [M−H]⁻.

EXAMPLE 6

2-((4-(Hydroxymethyl)-3-(trifluoromethyl)-1H-pyrazol-1-yl)methyl)-3,6-dimethylthieno[2,3-d]pyrimidin-4(3H)-one

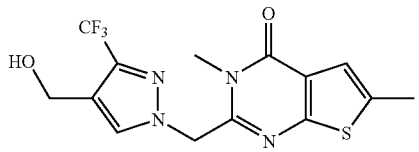

2-((4-(Hydroxymethyl)-3-(trifluoromethyl)-1H-pyrazol-1-yl)methyl)-6-methylthieno[2,3-d]pyrimidin-4(3H)-one (240 mg, 0.697 mmol) was dissolved in DMF (5 mL). NaH (17 mg, 0.708 mmol) was added and the reaction mixture heated at 60° C. for 1 h, then allowed to cool to RT before cooling further with an ice/salt bath to 0° C. Iodomethane (1.14 g, 0.50 mL, 8.03 mmol) was added in one portion and the reaction mixture stirred at RT for 1 h, then allowed to warm to RT, before standing overnight. The reaction mixture was acidified with 2M HCl and extracted into EtOAc (×3). The EtOAc layer was washed with brine, dried over MgSO₄, filtered and concentrated in vacuo. Purification by preparative reverse phase HPLC gave the title product as a white solid (76 mg, 0.213 mmol, 31%).

MS (ESI): 359 m/z [M+H]⁺.

EXAMPLE 7

6-Methyl-2-((4-((pyridin-3-ylmethylamino)methyl)-3-(trifluoromethyl)-1H-pyrazol-1-yl)methyl)thieno[2,3-d]pyrimidin-4(3H)-one

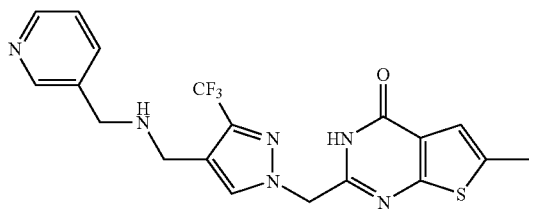

A solution of 3-(aminomethyl)pyridine (47 mg, 0.438 mmol) and 1-((6-methyl-4-oxo-3,4-dihydrothieno[2,3-a]pyrimidin-2-yl)methyl)-3-(trifluoromethyl)-1H-pyrazole-4-carbaldehyde (30 mg, 0.088 mmol) in NMP (3 mL), together with 10% AcOH in NMP (200 µl), was shaken for 30 min before the addition of sodium triacetoxyborohydride (93 mg, 0.438 mmol). The resultant mixture was shaken overnight. The mixture was quenched by addition of 1:1 AcOH:MeOH (200 µl), filtered through cotton wool and purified by preparative LCMS. The sample was then passed down an SCX cartridge, eluting with 7M NH₃ in MeOH (5 mL) to give the title product as a white solid (27 mg, 0.063 mmol, 12%).

MS (ESI): 435 m/z [M+H]⁺.

EXAMPLE 8

6-Methyl-2-((4-((thiazol-5-ylmethylamino)methyl)-3-(trifluoromethyl)-1H-pyrazol-1-yl)methyl)thieno[2,3-d]pyrimidin-4(3H)-one

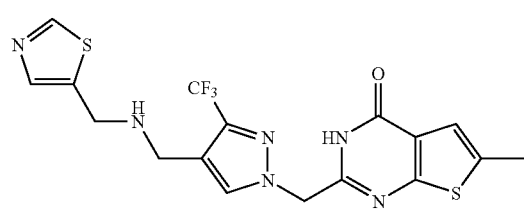

In a similar manner to example 7, thiazole-5-yl-methylamine hydrochloride (50 mg, 0.438 mmol) was used in place of 3-(aminomethyl)pyridine to yield the title compound (7 mg, 0.015 mmol, 17%).

MS (ESI): 441 m/z [M+H]⁺.

EXAMPLE 9

2-((4-(((1H-Benzo[d]imidazol-2-yl)methylamino)methyl)-3-(trifluoromethyl)-1H-pyrazol-1-yl)methyl)-6-methylthieno[2,3-d]pyrimidin-4(3H)-one

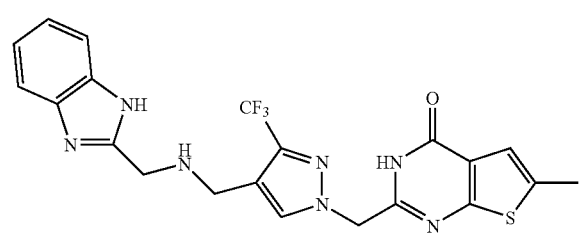

In a similar manner to example 7, 2-(aminomethyl)benzimidazole dihydrochloride hydrate (65 mg, 0.438 mmol) was used in place of 3-(aminomethyl)pyridine to yield the title compound (10 mg, 0.021 mmol, 24%).

MS (ESI): 474 m/z [M+H]⁺.

EXAMPLE 10

2-((4-(((1H-Imidazol-2-yl)methylamino)methyl)-3-(trifluoromethyl)-1H-pyrazol-1-yl)methyl)-6-methylthieno[2,3-d]pyrimidin-4(3H)-one

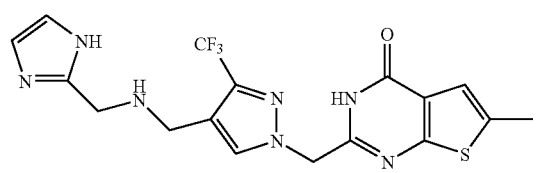

In a similar manner to example 7, 1H-imidazol-2-yl methylamine (50 mg, 0.511 mmol) was used in place of 3-(aminomethyl)pyridine to yield the title compound (8 mg, 0.019 mmol, 18%).

MS (ESI): 424 m/z [M+H]⁺.

EXAMPLE 11

2-((4-(Hydroxymethyl)-3-(trifluoromethyl)-1H-pyrazol-1-yl)methyl)-6-methyl-5-phenylthieno[2,3-d]pyrimidin-4(3H)-one a) 1-((6-Methyl-4-oxo-5-phenyl-3,4-dihydrothieno[2,3-d]pyrimidin-2-yl)methyl)-3-(trifluoromethyl)-1H-pyrazole-4-carbaldehyde

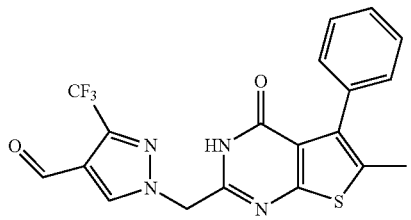

To a stirred suspension of 3-(trifluoromethyl)-1H-pyrazole-4-carbaldehyde (100 mg, 0.609 mmol) and potassium tert-butoxide (137 mg, 1.22 mmol) in THF (3 mL) was added 2-(chloromethyl)-6-methyl-5-phenylthieno[2,3-d]pyrimidin-4(3H)-one (177 mg, 0.609 mmol) and the resultant solution was stirred at RT for 2 days. The reaction mixture was quenched with water and concentrated in vacuo to give the crude product as a beige solid (97 mg, 0.232 mmol, 38%). The material was used without further purification.

b) 2-((4-(Hydroxymethyl)-3-(trifluoromethyl)-1H-pyrazol-1-yl)methyl)-6-methyl-5-phenyl thieno[2,3-d]pyrimidin-4(3H)-one

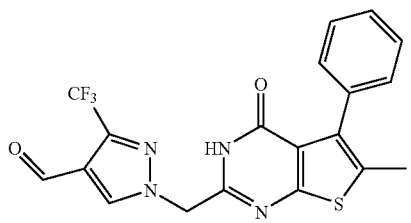

To a stirred solution of 1-((6-methyl-4-oxo-5-phenyl-3,4-dihydrothieno[2,3-d]pyrimidin-2-yl)methyl)-3-(trifluoromethyl)-1H-pyrazole-4-carbaldehyde (97 mg, 0.232 mmol) in DCM (2 mL) and MeOH (2 mL) was added sodium borohydride (26 mg, 0.696 mmol) and the mixture was stirred overnight. Sodium borohydride (53 mg, 1.39 mmol) was added and the mixture was stirred for a further 20 h. The reaction mixture was quenched with water and concentrated in vacuo. The residue was taken up in 1:1 DMSO:MeCN, filtered and purified by preparative LCMS to give the title product as a white solid (10 mg, 0.024 mmol, 10%).

MS (ESI): 421 m/z [M+H]⁺.

EXAMPLE 12

2-((4-(2-(1H-Imidazol-1-yl)ethyl)-3-(trifluoromethyl)-1H-pyrazol-1-yl)methyl)-6-methylthieno[2,3-d]pyrimidin-4(3H)-one a) 2-(1-((6-Methyl-4-oxo-3,4-dihydrothieno[2,3-d]pyrimidin-2-yl)methyl)-3-(trifluoromethyl)-1H-pyrazol-4-yl)ethyl methanesulfonate

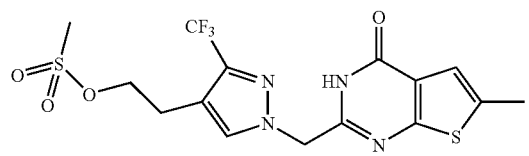

2-((4-(2-Hydroxyethyl)-3-(trifluoromethyl)-1H-pyrazol-1-yl)methyl)-6-methylthieno[2,3-d]pyrimidin-4(3H)-one (1.99 g, 5.55 mmol) was completely dissolved in pyridine (0.44 g, 20 mL, 5.55 mmol) and cooled in an acetone/sodium chloride/ice bath. Internal temperature was maintained at −10° C. Mesyl chloride (2.07 g, 1.40 mL, 18.1 mmol) was added portionwise and the temperature exothermed to 0° C. The mixture was stirred for 1 h at 0° C. and deionised water was added until solid precipitated out. The reaction was filtered, washed with water, and concentrated in vacuo to give the title compound as a pale yellow solid (2.11 g, 4.83 mmol, 87%).

MS (ESI): 437 m/z [M+H]⁺.

b) 2-((4-(2-(1H-Imidazol-1-yl)ethyl)-3-(trifluoromethyl)-1H-pyrazol-1-yl)methyl)-6-methyl thieno[2,3-a]pyrimidin-4(3H)-one

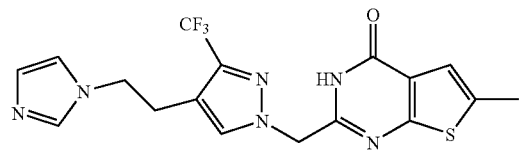

2-(1-((6-Methyl-4-oxo-3,4-dihydrothieno[2,3-d]pyrimidin-2-yl)methyl)-3-(trifluoromethyl)-1H-pyrazol-4-yl)ethyl methanesulfonate (150 mg, 0.344 mmol), 1H-imidazole (23 mg, 0.344 mmol) and potassium tert-butoxide (116 mg, 1.03 mmol) were dissolved in DMSO (3 mL) and the resulting mixture heated to 70° C. for 30 min by microwave irradiation. LCMS analysis of the crude mixture indicated incomplete reaction, so the mixture was heated to 100° C. for 1 h by microwave irradiation. The mixture was filtered and purified by preparative LCMS. The sample was then passed down an SCX cartridge, eluting with 2M NH₃ in MeOH to give the title product (15 mg, 0.037 mmol, 11%).

MS (ESI): 409 m/z [M+H]⁺.

EXAMPLE 13

N-((1-((6-methyl-4-oxo-3,4-dihydrothieno[2,3-d]pyrimidin-2-yl)methyl)-3-(trifluoromethyl)-1H-pyrazol-4-yl)methyl)acetamide a) 2-((4-(aminomethyl)-3-(trifluoromethyl)-1H-pyrazol-1-yl)methyl)-6-methylthieno[2,3-d]pyrimidin-4(3H)-one

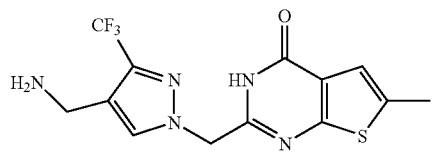

A solution of 1-((6-methyl-4-oxo-3,4-dihydrothieno[2,3-d]pyrimidin-2-yl)methyl)-3-(trifluoromethyl)-1H-pyrazole-4-carbaldehyde (2.92 mmol, 1 g) and hydroxylamine hydrochloride (3.21 mmol, 0.223 g) in ethanol (7 mL) was heated to 80° C. and this temperature was maintained for 3 h. The reaction mixture was allowed to cool to room temperature & diluted with ether and heptane before the resulting precipitate was collected by filtration. The resulting solid was taken up in acetic acid (5 mL) and zinc (7.79 mmol, 0.510 g) and the whole was stirred at room temperature for 3 days with occassional agitation by sonication. The reaction mixture was filtered through celite and the pad washed with MeOH before the filtrate was concentrated under reduced pressure. The residue was dissolved in MeOH and applied to an SCX cartridge that had been equilibrated with the same solvent before being eluted with 2N $NH_3$/MeOH to give a light yellow solid (271 mg, 0.79 mmol, 50.6%)

MS (ESI): 344 m/z $[M+H]^+$.

b) N-((1-((6-methyl-4-oxo-3,4-dihydrothieno[2,3-d]pyrimidin-2-yl)methyl)-3-(trifluoromethyl)-1H-pyrazol-4-yl)methyl)acetamide

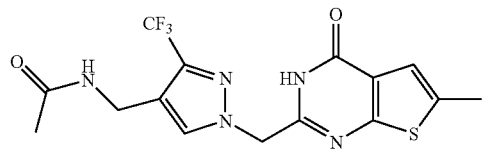

To a solution of 2-((4-(aminomethyl)-3-(trifluoromethyl)-1H-pyrazol-1-yl)methyl)-6-methylthieno[2,3-d]pyrimidin-4(3H)-one (0.087 mmol, 30 mg) and DIPEA (0.175 mmol, 0.029 ml, 22.59 mg) in DCM (1 mL) was added acetyl chloride (0.175 mmol, 0.012 ml, 13.72 mg). The whole was stirred at room temperature overnight before the reaction mixture was concentrated under reduced pressure and the residue purified by reverse phase HPLC to give a white solid (8.7 mg, 23 mmol. 25.8%)

MS (ESI): 386 m/z $[M+H]^+$.

EXAMPLE 14

2-((3-(hydroxymethyl)-4-(trifluoromethyl)-1H-pyrrol-1-yl)methyl)-6-methylthieno[2,3-d]pyrimidin-4(3H)-one a) methyl-4-(trifluoromethyl)-1H-pyrrole-3-carboxylate

In a 50 mL round bottomed flask was added sodium hydride (3.24 mmol, 78 mg) in $Et_2O$ (5 mL). A mixture of p-toluenesulfonylmethylisocyanide (3.24 mmol, 634 mg) and (E)-methyl-4,4,4-trifluoromethylbut-2-enoate (3.24 mmol, 500 mg) were added in a 2:1 mixture of $Et_2O$/DMSO (15 mL:7.5 mL). This became slightly warm and was stirred for 30 min. $H_2O$ (10 mL) was added and the reaction mixture extracted with $Et_2O$ (3×20 mL). The combined $Et_2O$ layers were washed with brine, dried over $MgSO_4$, filtered and the solvent removed under reduced pressure to give crude product (590 mg) as a yellow/orange solid. Purification by flash silica chromatography column (eluent 1:4 EtOAc:heptane) gave desired product (154 mg, 0.797 mmol, 25%)

$^1$H NMR (400 MHz, MeOD): δ 3.79 (s, 3H), 7.20 (s, 1H), 7.50 (s, 1H)

b) 2-((3-(hydroxymethyl)-4-(trifluoromethyl)-1H-pyrrol-1-yl)methyl)-6-methylthieno[2,3-d]pyrimidin-4(3H)-one

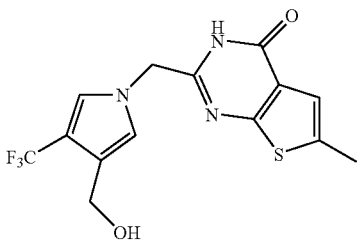

In a vial was added methyl-4-(trifluoromethyl)-1H-pyrrole-3-carboxylate (0.129 mmol, 25 mg) and sodium hydride (60% dispersion in oil, 0.432 mmol, 10.4 mg) in DMF (2 mL). 2-(chloromethyl)-6-methylthieno[2,3-a]pyrimidin-4(3H)-one (0.129 mmol, 27.8 mg) was added. The reactants were heated at 65° C. for 3 h then allowed to cool to room temp and left to stand overnight. $H_2O$ (10 mL) was added and the reaction mixture extracted into EtOAc (3×10 mL). The combined EtOAc layers were washed with brine, dried over $MgSO_4$, filtered and the solvent removed under reduced pressure to give crude intermediate. This was dissolved in THF (5 mL) and a solution of $LiAlH_4$ in THF added (2M, 1.295 mmol, 0.65 mL). The reaction mixture was stirred at room temp for 2 h then MeOH (5 mL) was added carefully and then stirred at room temp for 30 min. The solvent was removed under reduced pressure to give crude product which was purified by HPLC to give the desired product (2.5 mg, 7.3 µmol, 6%)

MS (ESI): 344 m/z $[M+H]^+$.

EXAMPLE 15

Biological Assays

A: $Ca^{2+}$ Influx Fluorescence Assays

The compounds in this invention may be tested using a biological assay which measures $Ca^{2+}$ influx mediated through positive modulation of the AMPA (GluR1) receptor using standard techniques in the art such as, but not limited to, a FLEXstation (manufactured by Molecular Devices, Sunnyvale, Calif.). An optical readout using fluorescent probes is employed to measure ion channel dependent changes in intracellular ion concentration or membrane potential. The assay utilises the $Ca^{2+}$ conductance of functional homomeric GluR1(i) AMPA receptors to generate glutamate-dependent $Ca^{2+}$ responses. Influx of $Ca^{2+}$ through the ion channel is measured indirectly through an increase in intracellular $Ca^{2+}$ levels using the calcium sensitive dye such as, but not limited to, Fluo-3 (Molecular Devices, Sunnyvale, Calif.) in FLEXstation. A positive AMPA receptor modulator, in the presence of glutamate, will result in an influx of $Ca^{2+}$ through the ion channel which can be measured indirectly through an increase in intracellular $Ca^{2+}$ levels using the calcium sensitive dye Fluo-3 in FLEXstation.

HEK.GluR1(i) cells were maintained in DMEM supplemented with 10% fetaclone II, 1% non-essential amino acids and 150 µg/mL hygromycin, at 37° C./5% CO2. Twenty-four h prior to the assay, the cells are harvested with trypsin and seeded onto Costar 96 well clear bottomed black plates at a density of $3.5 \times 10^4$ per well.

Cells are loaded with 5 µM fluo3-AM in DMEM media in the absence of hygromycin and incubated at 37° C./5% $CO_2$ for one h. After dye loading, the cells are washed once with 200 µl of low calcium solution (10 mM hepes, pH 7.4, 160 mM NaCl, 4.5 mM KCl, 2 mM $CaCl_2$, 1 mM $MgCl_2$, 10 mM glucose) containing 0.625 mM of probenecid (inhibitor for the anion-exchange protein) to remove the dye. Then 200 µl of low calcium solution is added to each well. The Flexstation adds 50 µl of glutamate +/−test compound in high calcium solution (10 mM Hepes, pH 7.4, 160 mM NaCl, 4.5 mM KCl, 20 mM $CaCl_2$, 1 mM $MgCl_2$ and 10 mM glucose) to each well and the ensuing response is monitored on FLEXstation.

The compounds of this invention exhibit positive modulation of the AMPA receptor having $EC_{50}$ values in the range 0.3 µM to 30 µM. For instance, Example 1 gave an $EC_{50}$ of 1 µM.

B: Patch Clamp Recording.

The whole cell configuration of the patch clamp technique (Hamill et al., Pflugers Arch. 1981, 39, 85-100) was used to measure glutamate-evoked currents from postnatal rat cortical neurones. A glass coverslip containing the culture was transferred to the recording chamber (Warner Instrument Corp., Hamden, Conn.) mounted on the stage of an inverted microscope (Nikon, Kingston, UK). The recording chamber contained 1-2 ml extracellular solution (145 mM NaCl, 5.4 mM KCl, 10 mM HEPES, 0.8 mM $MgCl_2$, 1.8 $CaCl_2$, 10 mM glucose and 30 mM sucrose, adjusted to pH 7.4 with 1M NaOH) and was constantly perused at a rate of 1 ml/min. Recordings were performed at room temperature (20-22° C.) using an Axopatch 200B amplifier (Axon Instruments Ltd., Foster City, Calif.). Data acquisition and analysis was performed using Signal software (Cambridge Electronic Design Ltd., Cambridge, UK). Pipettes were manufactured from GC120F-10 glass (Harvard Apparatus, Edenbridge UK) using a model P-87 electrode puller (Sutter Instruments Co., Novarto, Calif.). The patch electrodes had typical resistances of between 3-5 MQ when filled with intracellular solution (140 mM potassium gluconate, 20 mM HEPES, 1.1 mM EGTA, 5 mM phosphocreatine, 3 mM ATP, 0.3 mM GTP, 0.1 mM Caca2, 5 mM $MgCl_2$, adjusted to pH 7.4 with 1M KOH).

Cells were voltage clamped at a holding potential of −60 mV and glutamate (0.5 mM) was applied using a 12 channel semi-rapid drug application device (DAD-12. Digitimer Ltd., Welwyn Garden city, UK). The agonist glutamate was applied for 1 s every 30 s. The response did not "run-down" over time using the whole-cell configuration. Between applications saline flowed to clear any dead volume in the system. For each application steady-state currents were plotted from the difference in baseline and steady state current and averaged over 300 ms.

Two solutions of the compound in extracellular solution were made up, one with glutamate and one without. The protocol was: 10 second application of compound, 1 second application of compound+glutamate and then 10 second wash with saline, then a 10 second delay. When the compound was not soluble, 0.5% DMSO was used as a cosolvent. Results were calculated as the percentage increase in steady state current at 10 pM concentration of the compound of the invention in extracellular solution. Using this technique, Example 1 showed 235±44% increase in steady state current at 10 µM

We claim:

1. A heterocyclic compound according to formula I

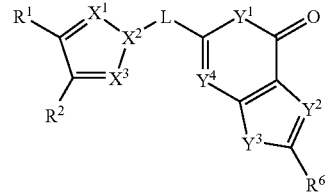

formula I wherein

L is $(CH_2)_m$, wherein m is 1 or 2;

$R^1$ is $C_{1-4}$alkyl, $C_{3-5}$cycloalkyl, $C_{1-4}$alkyloxy, halogen or CN, said $C_{1-4}$alkyl, $C_{3-5}$cycloalkyl and $C_{1-4}$alkyloxy being optionally substituted with one or more halogens;

$R^2$ is $C_{1-4}$alkyl, $C_{3-5}$cycloalkyl or $C_{1-4}$alkyloxy, said $C_{1-4}$alkyl, $C_{3-5}$cycloalkyl and $C_{1-4}$alkyloxy being substituted with a substituent selected from OH, $C_{1-4}$alkyloxy and $NR^9R^{10}$;

$X^1$, $X^2$ or $X^3$ are independently N or $CR^3$, wherein $R^3$ is H or methyl;

$Y^1$ is $NR^4$, wherein $R^4$ is H or $C_{1-4}$alkyl;

$Y^2$ is $CR^5$, wherein $R^5$ is H, $C_{1-4}$alkyl, $C_{3-8}$cycloalkyl or $C_{6-10}$aryl;

$R^6$ is H, $C_{1-4}$alkyl or $C_{3-5}$cycloalkyl;

$Y^3$ is S;

$Y^4$ is N;

$R^9$ and $R^{10}$ are independently H or $C_{1-4}$alkyl optionally substituted with a 5-9 membered heteroaryl ring system comprising 1-2 heteroatoms selected from O, S and N, or $R^9$ and $R^{10}$ together with the N to which they are bonded form a 4-6 membered saturated or unsaturated heterocyclic ring optionally comprising another heteroatom selected from O, S and N;

or a pharmaceutically acceptable salt thereof.

2. The heterocyclic compound according to claim 1, wherein R¹ is CF₃.

3. The heterocyclic compound according to claim 1, wherein R² is methyl optionally substituted with hydroxy or NR⁹R¹⁰.

4. The heterocyclic compound according to claim 1, wherein X¹ and X² are N and X³ is CH.

5. The heterocyclic compound according to claim 1, wherein Y¹ is NR⁴ and R⁴ is H or methyl.

6. The heterocyclic compound according to claim 1, wherein Y² is CR⁵ and R⁵ is H or methyl.

7. The heterocyclic compound according to claim 1, wherein R⁶ is H or methyl.

8. The heterocyclic compound according to claim 1, wherein m is 1.

9. A heterocyclic compound selected from:

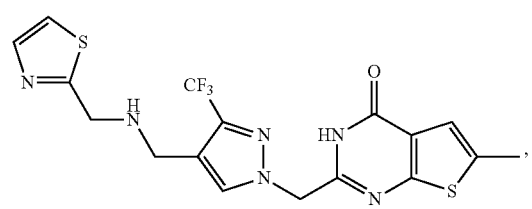

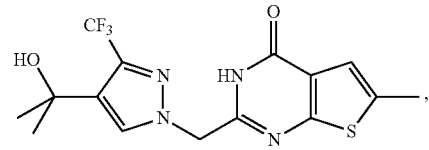

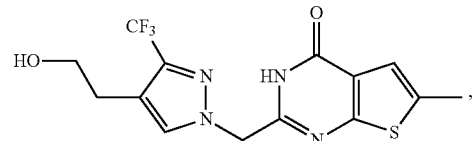

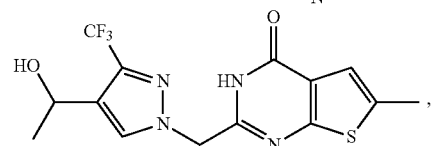

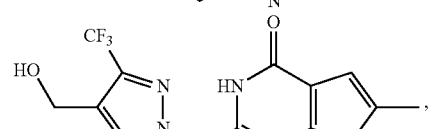

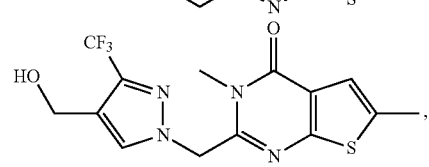

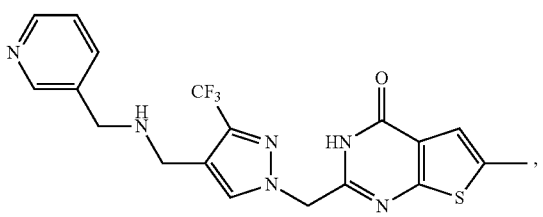

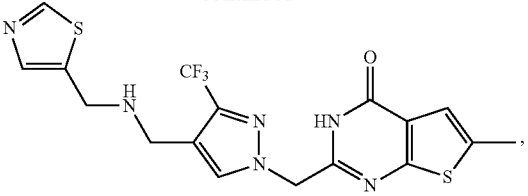

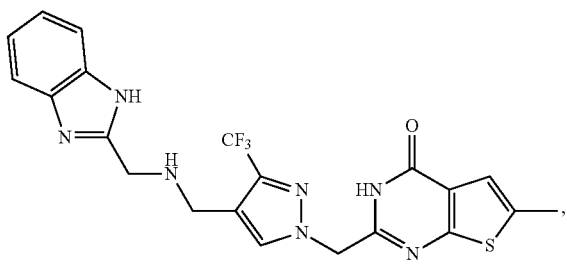

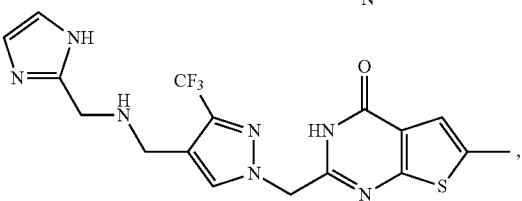

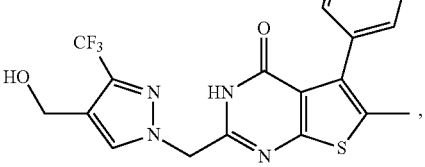

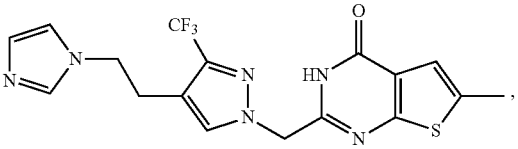

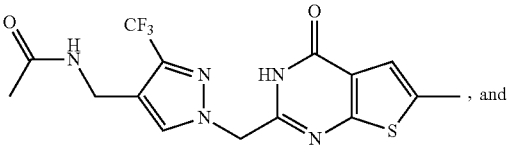

, and

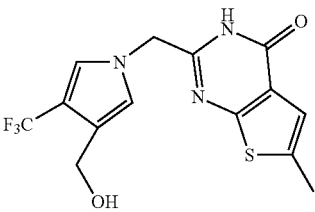

or a pharmaceutically acceptable salt thereof.

10. The heterocyclic compound of claim 9, wherein the heterocyclic derivative is

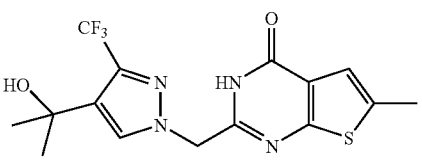

or a pharmaceutically acceptable salt thereof.

11. The heterocyclic compound of claim 9, wherein the heterocyclic derivative is

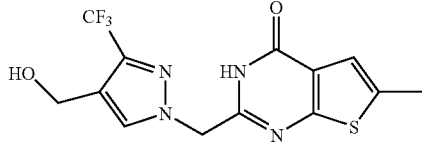

or a pharmaceutically acceptable salt thereof.

12. A pharmaceutical composition comprising a heterocyclic compound or a pharmaceutically acceptable salt thereof according to claim 1 in admixture with one or more pharmaceutically acceptable auxiliaries.

13. A pharmaceutical composition according to claim 12, wherein the heterocyclic compound is selected from the group consisting of

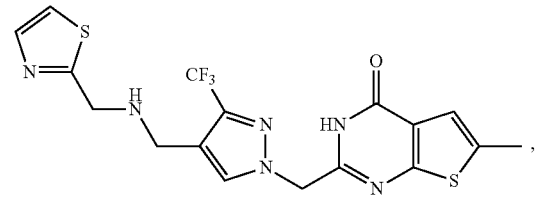

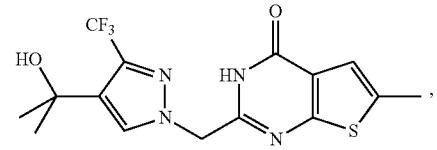

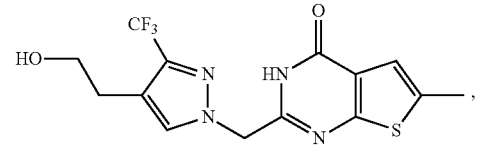

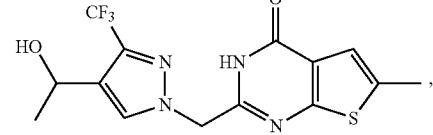

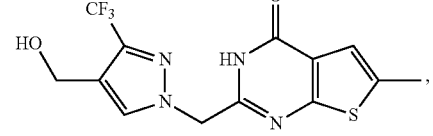

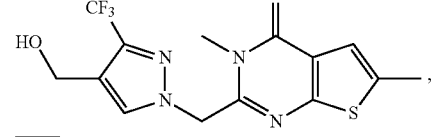

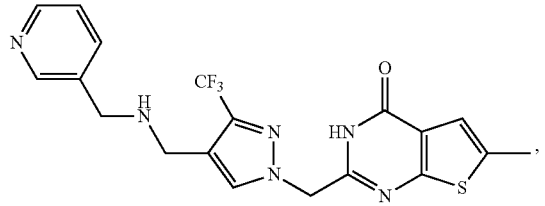

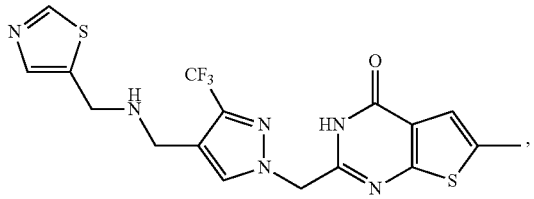

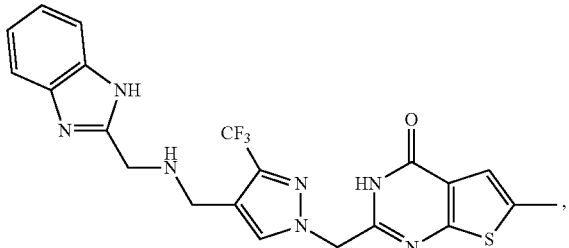

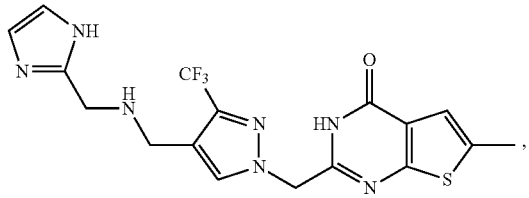

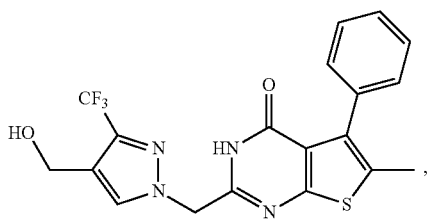

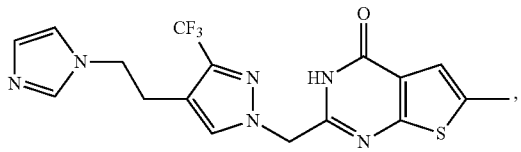

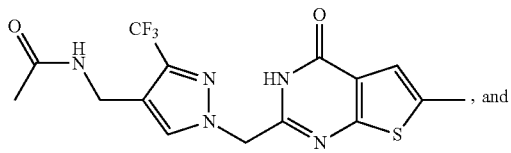

, and

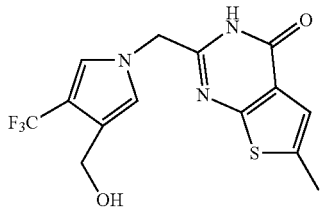

or a pharmaceutically acceptable salt thereof, in admixture with one or more pharmaceutically acceptable auxiliaries.

14. The pharmaceutical composition according to claim 13, wherein the heterocyclic compound is
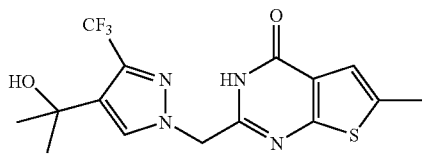
or a pharmaceutically acceptable salt thereof.
15. The pharmaceutical composition according to claim 13, wherein the heterocyclic compound is
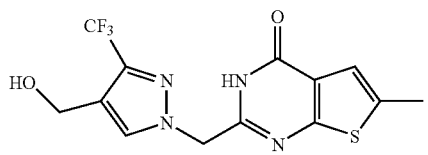
or a pharmaceutically acceptable salt thereof.
* * * * *